United States Patent [19]
Ochiai et al.

[11] 4,250,193
[45] Feb. 10, 1981

[54] COSMETICS

[75] Inventors: Michio Ochiai, Yokohama; Noriaki Tonooka; Kenkichi Matubara, both of Yokosuka, all of Japan

[73] Assignee: Pola Chemical Industries, Inc., Shizuoka, Japan

[21] Appl. No.: 922,112

[22] Filed: Jul. 5, 1978

[30] Foreign Application Priority Data

Jul. 5, 1977 [JP] Japan ................................ 52/79541

[51] Int. Cl.³ ............................................... A61K 7/48
[52] U.S. Cl. ...................................... 424/358; 424/70; 424/73; 424/361
[58] Field of Search .............................. 424/358, 342; 260/615 B

[56] References Cited

U.S. PATENT DOCUMENTS

| 2,089,569 | 8/1937 | Orthner et al. | 260/615 B |
| 2,236,919 | 4/1941 | Reynhart | 260/615 B |
| 2,253,723 | 8/1941 | Moore | 260/615 B |
| 2,258,892 | 10/1941 | Harris | 424/358 |
| 2,302,121 | 11/1942 | Harris | 424/358 |
| 2,327,053 | 8/1943 | Marple et al. | 260/615 B |
| 2,380,185 | 7/1945 | Marple et al. | 260/615 B |
| 2,425,755 | 8/1947 | Roberts et al. | 260/615 B |
| 2,450,079 | 9/1948 | Brown | 260/615 B |
| 2,554,667 | 5/1951 | De Groote | 260/615 B X |
| 2,679,520 | 5/1954 | De Groote | 260/615 B X |
| 2,679,521 | 5/1954 | De Groote | 260/615 B X |
| 2,723,285 | 11/1955 | DeGroote | 260/615 B |
| 3,081,354 | 3/1963 | Gaertner | 260/615 B |
| 3,110,736 | 11/1963 | De Groote et al. | 424/342 X |
| 3,110,737 | 11/1963 | De Groote et al. | 424/342 X |
| 3,932,532 | 1/1976 | Hunter et al. | 424/342 |
| 3,959,390 | 5/1976 | Vanlerberghe | 260/615 R |
| 4,086,279 | 4/1978 | Langdon et al. | 260/615 B |
| 4,087,466 | 5/1978 | Vanlerberghe et al. | 260/615 B |

FOREIGN PATENT DOCUMENTS

| 491673 | 3/1953 | Canada | 260/615 B |
| 545116 | 8/1957 | Canada | 260/615 B |
| 577316 | 6/1959 | Canada | 260/615 B |
| 652869 | 11/1962 | Canada | 260/615 B |
| 1169272 | 11/1969 | United Kingdom | 260/615 B |

Primary Examiner—Dale R. Ore
Attorney, Agent, or Firm—Kurt Kelman

[57] ABSTRACT

Disclosed are cosmetics containing an oily bisdiglyceryl ether compound. This novel compound can be prepared by adding an alkylene glycol, dialkylene glycol, trialkylene glycol or tetraalkylene glycol dropwise to an alkylglycidyl ether using as a catalyst a boron trifluoride ether complex, other Lewis acid, sodium hydroxide or potassium hydroxide and removing the catalyst with the use of sodium carbonate, calcium carbonate, potassium carbonate, these aqueous solutions or water upon heating, followed by rectification of the resultant oily liquid under reduced pressures. The cosmetics of this type do not cause any dermatitis or skin disease due to the absence of surface active agents.

4 Claims, No Drawings

COSMETICS

BACKGROUND OF THE INVENTION

The present invention relates to cosmetics containing an oily bidiglyceryl ether compound, and has for its object to provide novel cosmetics which are free from any stimulating action of surface active agents exercised on the skin, are virtually stable with respect to hydrolysis and can endow the skin with proper wettability and softening action.

Oily solvents used in cosmetics are generally selected from fats and oils (triglyceride), waxes, higher alcohols, higher fatty acids, hydrocarbons, esters and the like. Most of the oily solvents that have been heretofore known are not easily dissolved in water-alcohol based cosmetics having an alcohol content of less then 50%, i.e., lotions such as toilet lotions, cosmetic removers, hair tonics, cleansers and body lotions. While castor oil, isopropyl myristate (hereinafter referred to as I.P.M.), oleyl alcohol, hexadecyl alcohol etc. are exceptionally employed in such lotions, they can be added thereto only in small amounts due to their poor solubility with the result that no proper wettability is given to the skin. Furthermore, when it is desired to add fats and oils to the cosmetics having a smaller alcohol content such as cosmetic removers, they need to be solubilized with the aid of a specific surface active agent having a relatively high HLB (the average HLB nearly equals 15). However, the use of such a surface active agent is responsible for a variety of dermatitis recently caused by cosmetics and consequently disadvantageous. A compound of a dibasic ester type such as polypropylene glycol malate is also known. However, such a compound tends to undergo hydrolysis with time in a water-alcohol system, resulting in a change in quality and hence unsatisfactory stability.

As a consequence of extensive investigations performed from the foregoing viewpoint, we have found a novel compound which is easily dissolved in water-alcohol based cosmetics, is well compatible with other oily solvents and is extremely stable in a water-alcohol system without suffering substantial hydrolysis.

SUMMARY OF THE INVENTION

The present invention relates to cosmetics containing preferably 3 to 20% of an oily bisdiglyceryl ether compound having the general formula:

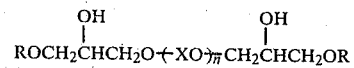

wherein X represents an alkylene group having 2 to 5 carbon atoms, n is an integral number 1 to 4 and R stands for an alkyl group having 1 to 5 carbon atoms.

DETAILED DESCRIPTION OF THE INVENTION

As the novel compounds which may be applied in the present invention, mentioned are bis-(ethylglyceryl)-ethylene ether, bis-(propylglycerol)-tetraethylene ether, bis-(amylglyceryl)-tetramethylene ether, bis-(ethylglyceryl)-diethylene glycol ether, bis-(butylglyceryl)-diethylene glycol ether, bis(amylglyceryl)-diethylene glycol ether, bis(ethylglyceryl)-triethylene glycol ether, bis-(ethylglyceryl)-tetraethylene glycol ether etc. These compound may be synthesized, for instance, by adding an alkylene glycol, dialkylene glycol, trialkylene glycol or tetraalkylene glycol such as ethylene glycol, diethylene glycol, triethylene glycol or tetraethylene glycol dropwise to an alkylglycidyl ether such as methylglycidyl ether using as a catalyst a boron trifluoride ether complex or other Lewis acid such as stannic tetrachloride, aluminium chloride, alkali such as sodium hydroxide, potassium hydroxide or the like, preferably the boron trifluoride ether complex, and removing the catalyst with the use of sodium carbonate, calcium carbonate, potassium carbonate, these aqueous solutions, or water upon heating, followed by rectification of the resulting oily liquid under reduced pressures.

The solubility of each of the novel compounds Bis-(ethylglyceryl)-ethylene ether(A), Bis-(propylglyceryl)-triethylene ether(B), Bis-(propylglyceryl)-tetraethylene ether(C), Bis-(butylglyceryl)-triethylene ether(D), Bis-(ethylglyceryl)-diethylene glycol ether(E), Bis-(butylglyceryl)-diethylene glycol ether(F), Bis-(butylglyceryl)-triethylene glycol ether(G) and Bis-(amylglyceryl)-tetraethylene glycol ether(H) of the present invention as well as dipropylene glycol malate(I) and I.P.M.(J) which have been heretofore used as an oily solvent in cosmetics with respect to hydrous ethyl alcohol is set forth in Table I (the amount of each compond added: 10%). In this connection, it has been found that the solubility of each novel compound other than the compounds(A)~(H) is in a similar order.

TABLE I

| | Sample | Ethyl Alcohol Content (%) | | | | | | |
|---|---|---|---|---|---|---|---|---|
| | | 10 | 30 | 40 | 50 | 70 | 80 | 100 |
| (A) | Bis-(ethylglyceryl)-ethylene ether | O | O | O | O | O | O | O |
| (B) | Bis-(propylglyceryl)-triethylene ether | O | O | O | O | O | O | O |
| (C) | Bis-(propylglyceryl)-tetraethylene ether | O | O | O | O | O | O | O |
| (D) | Bis-(butylglyceryl)-triethylene ether | Δ | O | O | O | O | O | O |
| (E) | Bis-(ethylglyceryl)-diethylene glycol ether | O | O | O | O | O | O | O |
| (F) | Bis-(buthylglyceryl)-diethylene glycol ether | Δ | O | O | O | O | O | O |
| (G) | Bis-(buthylglyceryl)-triethylene glycol ether | O | O | O | O | O | O | O |
| (H) | Bis-(amylglyceryl)-tetraethylene glycol ether | Δ | Δ | O | O | O | O | O |
| (I) | Dipolypropylene glycol malate (the average molecular weight: about 700) | X | X | O | O | O | O | O |
| (J) | I.P.M. | X | X | X | X | X | O | O |

O: soluble
Δ: less soluble
X: insoluble

As will be apparent from Table 1, the novel compounds of the present invention are easily soluble in a water-alcohol system having a relatively low alcohol content. This ensures that it is unnecessary to solubilize such novel compounds with the aid of any specific surface active agent having a relatively high HLB such as polyoxy-ethylenelauryl ether which has a stimulating action on the skin and is responsible for skin diseases. Accordingly, the water-alcohol based cosmetics in which the novel compounds of the present invention are used as oily solvents are applied to the skin without fear of causing a skin-stimulating action or skin disease that is caused by such surface active agents. And according to hydrolysis tests lasting 90 minutes, with each of the novel compounds (A)~(H) of the present invention as well as dipropylene glycol malate (I) and I.P.M. (J) in basic alcohols aqueous solution (NaOH: $C_2H_5OH:H_2O=4:48:10$, reflux), the novel compounds (A)~(H) underwent no substantial hydrolysis. To the contrary, both (I) and (J) had at least more than 90% hydrolyzed. In this connection, it has been found that the hydrolysis of each compound other than the compounds (A)~(H) is in a similar order.

Some preparation examples of the novel compounds of the present invention will now be given.

Preparation Example 1

0.5 grams of a boron trifluoride ether complex were added to 31 grams of ethylene glycol and were fully mixed under agitation therewith. To the resultant mixture were gradually added dropwise 102 grams of ethylglycidyl ether at room temperature over a period of 9.5 hours. The resultant product was then heated at about 100° C. for 3 hours and was added with 10 grams of anhydrous sodium carbonate, followed by sufficient stirring and mixing. Thereafter, the undissolved matters were filtered off. The formed oily liquid was rectified under reduced pressures to obtain 78 grams of bis-(ethylglyceryl)-ethylene ether.

Preparation Example 2

0.5 grams of a boron trifluoride ether complex were added to 45 grams of 1.4-butanediol and were fully mixed under agitation therewith. To the resultant mixture were gradually added dropwise 116 grams of propylglycidyl ether at room temperature over a period of 8.5 hours. The resultant product was then heated at about 100° C. for 3 hours and was added with 10 grams of anhydrous calcium carbonate, followed by sufficient stirring and mixing. Thereafter, the undissolved matters were filtered off. The formed oily liquid was rectified under reduced pressures to obtain 72 grams of bis-(propylglyceryl)-tetramethylene ether.

Preparation Example 3

0.5 grams of a boron trifluoride ether complex were added to 45 grams of 1.4-butanediol and were sufficiently mixed under agitation therewith. To the resultant mixture were gradually added dropwise 114 grams of 2-propenylglycidyl ether at room temperature over a period of 10 hours. The resultant product was then heated at about 100° C. for 3 hours and was added with 50 cc of potassium carbonate solution, followed by sufficient stirring and mixing. Thereafter, the formed product from which the aqueous phase had been removed was rectified under reduced pressures to obtain 68 grams of bis-(2-propenylglyceryl)-tetramethylene ether.

Preparation Example 4

0.5 grams of sodium hydroxide were added to 51 grams of diethylene glycol and were fully mixed under agitation therewith. To the resultant mixture were gradually added dropwise 102 grams of ethylglycidyl ether at room temperature over a period of 9.5 hours. The resultant product was then heated at about 100° C. for 3 hours and was added with 10 grams of anhydrous sodium carbobate, followed by sufficient stirring and mixing. Thereafter the undissolved matters were filtered off. The formed oily liquid was rectified under reduced pressures to obtain 98 grams of bis-(ethylglyceryl)-diethylene glycol ether.

Preparation Example 5

0.5 grams of a boron trifluoride ether complex were added to 51 grams of diethylene glycol and were fully mixed under agitation therewith. To the resultant mixture were gradually added dropwise 130 grams of butylglycidyl ether at room temperature over a period of 8.5 hours. The resultant product was then heated at about 100° C. for 3 hours and was added with 10 grams of anhydrous calcium carbonate, followed by sufficient stirring and mixing. Thereafter, the undissolved matters were filtered off. The formed oily liquid was rectified under reduced pressures to obtain 95 grams of bis-(butylglyceryl)-diethylene glycol ether.

Preparation Example 6

0.5 grams of potassium hydroxide were added to 74 grams of triethylene glycol and were fully mixed under agitation therewith. To the resultant mixture were gradually added dropwise 130 grams of butylglycidyl ether at 100° C. over a period of 9.5 hours. The resultant product was at room temperature and was added with 100° cc of sodium carbonate solution, followed by sufficient stirring and mixing. Thereafter, the aqueous phase had been removed. The formed oily liquid was rectified under reduced pressures to obtain 102 grams of bis-(butylglyceryl)-triethylene glycol ether.

Preparation Example 7

0.5 grams of sodium hydroxide were added to 82 grams of tetraethylene glycol and were sufficiently mixed under agitation therewith. To the resultant mixture were gradually added dropwise 128 grams of amylglycidyl ether at 100° C. over a period of 10 hours. The resultant product was at room temperature and was added with 50 cc of water, followed by sufficient stirring and mixing. Thereafter, the formed product from which the aqueous phase had been removed was rectified under reduced pressures to obtain 81 grams of bis-(amylglyceryl)-tetraethylene glycol ether.

The cosmetics containing the novel compounds according to the present invention can endow the skin with the substantially same wettability as that inherent in cosmetics containing glycerol and the virtually same softening action as that characteristic of the cosmetics using mainly oily solvents. For example, the lotions containing the novel compounds according to the present invention such as toilet lotions, cosmetic removers, hair tonics, body lotions etc. can endow the skin with the touch and feel characteristic of such novel compound and not heretofore obtained, and are safely used. This is because no dermatitis and skin diseases are caused due to the absence of any surface agent. Furthermore, since the novel compounds used in the present invention do no undergo substantial hydrolysis, thus leading to no change in quality, they can be incorporated into a wide range of, for instance, the above-mentioned lotions to general-purpose cosmetics inclusive of gelated cosmetics. In particular, the compounds according to the present invention are effective for use in gelated cleansers making use of a cleansing force.

Table II shows the results of the organoleptic examination where 50 women used continuously the body lotion prepared according to Example 3 of the present invention to be described later and the conventional body lotion.

TABLE II

|  |  | Sample | |
| --- | --- | --- | --- |
|  |  | X | Y |
| Fitness to the skin | Very Good | 37 | 23 |
|  | Good | 13 | 15 |
|  | Bad | 0 | 12 |
|  | None | 40 | 35 |
| Stickiness | Less | 8 | 11 |
|  | Too Much | 2 | 4 |

TABLE II-continued

|  |  | Sample | |
|---|---|---|---|
|  |  | X | Y |
| Softening action | Very Good | 42 | 31 |
|  | Good | 6 | 14 |
|  | Bad | 2 | 5 |
| Durability (Softening action) | Very Good | 46 | 20 |
|  | Good | 4 | 21 |
|  | None | 0 | 9 |

X: Body lotion of Example 3
Y: Conventional body lotion in which bis-(butylglyceryl)-tetraethylene ether was substituted with hexadecyl alcohol.

The above results show that the body lotion of the present invention is superior to the conventional body lotion in all respects.

The following are some examples of the present invention in which the proportion of each component to be added is expressed in terms of weight percentage.

EXAMPLE 1—NUTRITIVE TOILET LOTION

| Component A | |
|---|---|
| Ethanol | 15 |
| Propylene glycol | 5 |
| Bis-(propylglyceryl)-triethylene ether | 5 |
| Polyoxyethylene-cured castor oil derivative | 0.4 |
| Perfume | 0.1 |
| Component B | |
| Refined water | 20 |
| Succinic acid | 0.25 |
| Sodium succinate | 0.05 |
| Component C | |
| Refined water | 54.2 |

To the components A dissolved at 60°–70° C. were gradually adde the components B at room temperature. The refined water C was then added to the resultant solution, followed by filtration at room temperature. Thus the product was formed.

EXAMPLE 2—COSMETIC REMOVER

| Component A | |
|---|---|
| Ethanol | 15 |
| Propylene glycol | 5 |
| Bis-(propylglyceryl)-tetraethylene ether | 10 |
| Polyoxyethylene-cured castor oil derivative | 0.5 |
| Perfume | 0.1 |
| Component B | |
| Refined water | 20 |
| Succinic acid | 0.25 |
| Sodium succinate | 0.05 |
| Component C | |
| Refined water | 49.1 |

The product was prepared in the same manner as in Example 1.

EXAMPLE 3—BODY LOTION

| Component A | |
|---|---|
| Hydroxylpropyl cellulose | 2 |
| Ethanol | 50 |
| Refined Water | 37.5 |
| Component B | |
| Bis-(butylglyceryl)-tetraethylene ether | 5 |
| Propylene glycol | 5 |
| Perfume | 0.5 |
| Pearl essence | minor amount |

The components A were stirred and dispersed by means of a stirrer to form a viscous solution, to which was, in turn, added under agitation the components B at room temperature. The product was then charged in a suitable container.

EXAMPLE 4—GELATED CLEANSER

| Component A | |
|---|---|
| Bis-(propylglyceryl)-tetraethylene ether | 20 |
| Ethanol | 15 |
| Propylene glycol | 10 |
| Polyoxyethylene-cured castor oil derivative | 0.5 |
| Perfume | 0.1 |
| Component B | |
| Carbopol (1% aqueous solution) | 45 |
| Component C | |
| Triethanol amine (10% aqueous solution) | 6 |
| Refined water | 4 |

The components A were dissolved at 60°–70° C. and cooled to 30° C., and were added with the components B and then C. The formed product was finished by cooling it to room temperature.

EXAMPLE 5—AFTER-SHAVE LOTION

| Component A | |
|---|---|
| Ethanol | 50 |
| Aluminium chloride | 0.1 |
| Bis-(butylglyceryl)-pentaethylene ether | 5 |
| Perfume | 0.3 |
| Component B | |
| Succinic acid | 0.25 |
| Sodium succinate | 0.05 |
| Refined water | 44.3 |

The components A were dissolved at room temperature and added with the components B, followed by filtration at room temperature. Thus the product was prepared.

EXAMPLE 6—HAIR TONIC

| Component A | |
|---|---|
| Ethanol | 70 |
| Component B | |
| Menthol | 0.4 |
| Salicylic acid | 0.1 |
| Propylene glycol | 4 |
| Cayenne tincture | 0.5 |
| Perfume | 3 |
| Bis-(amylglyceryl)-pentaethylene ether | 5 |
| Refined water | 17 |

The components B were successively added under agitation to the component A and were dissolved therein, followed by filtration at room temperature. Thus the product was prepared.

EXAMPLE 7—HAIR OIL

| Component A | |
|---|---|
| Bis-(amylglyceryl)-diethylene ether | 85 |
| Ethanol | 10 |
| Perfume | 3 |
| Polyoxyethylene polypropylene glycol | 2 |

The components A were successively dissolved by stirring and were subjected to filtration, thereby to form the product.

EXAMPLE 8—NUTRITIVE CREAM

| Component A | |
|---|---|
| Squalane | 5 |
| Bis-(amylglyceryl)-pentaethylene ether | 10 |
| Spermaceti | 2.5 |
| Cethanol | 1.5 |
| Lanolin | 3.0 |
| Stearic acid | 6.0 |
| Polyoxyethylene sorbitan monostearate | 4.5 |
| Sorbitan monostearate | 1.5 |
| Preservatives | minor amount |
| Perfume | 1.0 |
| Component B | |
| Refined water | 65 |

The components A were dissolved at 80°–85° C. and were maintained at 80° C. To the resulting solution was gradually added under agitation the component B which had separately been heated to 80° C. Upon the addition, the resulting product was cooled to 25° C. and was allowed to stand for 10 days. Thereafter, the product was charged in a suitable container.

EXAMPLE 9—NUTRITIVE TOILET LOTION

| Component A | |
|---|---|
| Ethanol | 15 |
| Propylene glycol | 5 |
| Bis-(butylglyceryl)-triethylene glycol ether | 5 |
| Polyoxyethylene-cured castor oil derivative | 0.4 |
| Perfume | 0.1 |
| Component B | |
| Refined water | 20 |
| Succinic acid | 0.25 |
| Sodium succinate | 0.05 |
| Component C | |
| Refined water | 54.2 |

To the components A dissolved at 60°–70° C. were gradually added the components B at room temperature. The refined water C was then added to the resultant solution, followed by filtration at room temperature. Thus the product was formed.

EXAMPLE 10—COSMETIC REMOVER

| Component A | |
|---|---|
| Ethanol | 15 |
| Propylene glycol | 5 |
| Bis-(ethylglyceryl)-diethylene glycol ether | 10 |
| Polyoxyethylene-cured castor oil derivative | 0.5 |
| Perfume | 0.1 |
| Component B | |
| Refined water | 20 |
| Succinic acid | 0.25 |
| Sodium succinate | 0.05 |
| Component C | |
| Refined water | 49.1 |

The product was prepared in the same manner as in Example 1.

EXAMPLE 11—BODY LOTION

| Component A | |
|---|---|
| Hydroxylpropyl cellulose | 2 |
| Ethanol | 50 |
| Refined Water | 37.5 |
| Component B | |
| Bis-(methylglyceryl)-dipentalene glycol ether | 5 |
| Propylene glycol | 5 |
| Perfume | 0.5 |
| Pearl essence | minor amount |

The components A were stirred and dispersed by means of a stirrer to form a viscous solution, to which was, in turn, added under agitation the components B at room temperature. The product was then charged in a suitable container.

EXAMPLE 12—GELATED CLEANSER

| Component A | |
|---|---|
| Bis-(butylglyceryl)-diethylene glycol ether | 20 |
| Ethanol | 15 |
| Propylene glycol | 10 |
| Polyoxyethylene-cured castor oil derivative | 0.5 |
| Perfume | 0.1 |
| Component B | |
| Carbopol (1% aqueous solution) | 45 |
| Component C | |
| Triethanolamine (10% aqueous solution) | 6 |
| Refined water | 4 |

The components A were dissolved at 60°–70° C. and cooled to 30° C., and were added with the components B and then C. The formed product was finished by cooling it to room temperature.

EXAMPLE 13—AFTER-SHAVE LOTION

| Component A | |
|---|---|
| Ethanol | 50 |
| Aluminium chloride | 0.1 |
| Bis-(amylglyceryl)-tetraethylene glycol ether | 5 |
| Perfume | 0.3 |
| Component B | |
| Succinic acid | 0.25 |
| Sodium succinate | 0.05 |
| Refined water | 44.3 |

The components A were dissolved at room temperature and added with the components B, followed by filtration at room temperature. Thus the product was prepared.

EXAMPLE 14—HAIR TONIC

| Component A | |
|---|---|
| Ethanol | 70 |
| Component B | |
| Menthol | 0.4 |
| Salicylic acid | 0.1 |
| Propylene glycol | 4 |
| Cayenne tincture | 0.5 |
| Perfume | 3 |
| Bis-(amylglyceryl)-triethylene glycol ether | 5 |
| Refined water | 17 |

The components B were successively added under agitation to the component A and were dissolved therein, followed by filtration at room temperature. Thus the product was prepared.

EXAMPLE 15—HAIR OIL

| Component A | |
|---|---|
| Bis-(butylglyceryl)-tetraethylene | 85 |

| -continued | |
|---|---|
| glycol ether | |
| Ethanol | 10 |
| Perfume | 3 |
| Polyoxyethylene polypropylene glycol | 2 |

The components A were successively dissolved by stirring and were subjected to filtration, thereby to form the product.

EXAMPLE 16—NUTRITIVE CREAM

| Component A | |
|---|---|
| Squalane | 5 |
| Bis-(propylglyceryl)-dibutylene glycol ether | 10 |
| Spermaceti | 2.5 |
| Cethanol | 1.5 |
| Lanolin | 3.0 |
| Stearic acid | 6.0 |
| Polyoxyethylene sorbitan monostearate | 4.5 |
| Sorbitan monostearate | 1.5 |
| Preservatives | minor amount |
| Perfume | 1.0 |
| Component B | |
| Refined water | 65 |

The components A were dissolved at 80°–85° C. and were maintained at 80° C. To the resulting solution was gradually added under agitation the component B which had separately been heated to 80° C. Upon the addition, the resulting product was cooled to 25° C. and was allowed to stand for 10 days. Thereafter, the product was charged in a suitable container.

What is claimed is:

1. A cosmetic product for appalicatioan to the skin, and hair capable of endowing the skin and hair with wettability and softening action which comprises about 35–70% water, about 15–50% alcohol and about 5–20% of an oily bisdiglyceryl ether compound selected from the group consisting of bis-(propylglyceryl)-triethylene ether, bis-(propylglyceryl)-tetraethylene ether, bis-(butylglyceryl)-tetraethylene ether, bis-(butylglyceryl)-pentaetylene ether, bis-(butylglyceryl)-triethylene glycol ether, bis-(ethylglyceryl)-diethylene glycol ether, bis-(methylglyceryl)-dipentalene glycol ether, bis-(butylglyceryl)-diethylene glycol ether, bis-(amylglyceryl)-tetraethylene glycol ether and bis-(propylglyceryl)-dibutylene glycol ether, the compound being easily dissolved and remaining stable in the water-alcohol system.

2. A hair tonic comprising 17% water, 70% alcohol, 5% bis-(amylglyceryl)-pentaethylene ether or bis-(amylglyceryl)-triethylene glycol ether.

3. A hair oil comprising 85% bis-(amylglyceryl)-diethylene ether or bis-(butylglyceryl)-tetraethylene glycol ether and 10% alcohol.

4. A nutritive cream comprising 65% water and 10% bis-(amylglyceryl)-pentaethylene ether or bis-(propylglyceryl)-dibutylene glycol ether.

* * * * *